(12) United States Patent
Nakatani (10) Patent No.: US 6,542,084 B1
(45) Date of Patent: Apr. 1, 2003

(54) THERMAL ANALYZER (75) Inventor: Rintaro Nakatani, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/355,226

(22) PCT Filed: Nov. 25, 1998

(86) PCT No.: PCT/JP98/05308

§ 371 (c)(1),
(2), (4) Date: Oct. 15, 1999

(87) PCT Pub. No.: WO99/27354

PCT Pub. Date: Jun. 3, 1999

(30) Foreign Application Priority Data

Nov. 26, 1997 (JP) .............................. 9-325024

(51) Int. Cl.⁷ .............................................. G08B 21/00
(52) U.S. Cl. ................................. 340/870.16; 700/299
(58) Field of Search .................... 340/870.16; 700/274, 700/299, 300; 432/121, 128

(56) References Cited

U.S. PATENT DOCUMENTS

| | | | | | |
|---|---|---|---|---|---|
| 3,637,985 A | * | 1/1972 | Stacey | ......................... | 219/490 |
| 4,982,347 A | * | 1/1991 | Rackerby et al. | ............ | 700/299 |
| 5,228,778 A | | 7/1993 | Nakatani | ..................... | 374/33 |
| 5,448,504 A | | 9/1995 | Nakatani | ..................... | 364/557 |
| 5,582,235 A | * | 12/1996 | Hamilton et al. | ............ | 165/263 |
| 5,740,080 A | * | 4/1998 | Shook et al. | ............... | 700/299 |

* cited by examiner

Primary Examiner—Timothy Edwards, Jr.
(74) Attorney, Agent, or Firm—Adams & Wilks (57) ABSTRACT A thermal analyzer comprising a measurement module (8) having a heating furnace (1), a measurement station (16) which controls the measurement module (8) and has a measurement user interface, a monitor (24) and software operating on respective central processing units (6, 12 and 20). An inquiry made about the existence of data and transfer of user-designated data to the measurement stat ion (16) in which measurement data are stored from the monitor station (23) permits us to monitor the data at the monitor station (23).

27 Claims, 11 Drawing Sheets

THERMAL ANALYZER

TECHNICAL FIELD

The preset invention relates to a thermal analysis apparatuse.

BACKGROUND OF THE INVENTION

It can be pointed out that determination of thermal analysis properties take a long time in measurement time. The measurement usually requires several hours and, in a long case, may take several days. Meanwhile, during measurement it is not necessarily required for a user to be present close to a heating oven. In a case that a laboratory or the like placed with a heating oven and a sitting room or the like which are distant from each other for safety sake or the like, it has been a common practice for a user to be present in the laboratory when beginning measurement and to thereafter reciprocate between the laboratory and the sitting room to see data situations. Due to this, there has been a need to watch data during measurement from a sitting room or the like.

Conventionally, technologies for satisfying such demands included a network window system, such as X-Window, that is adopted for a user interface of a thermal analysis apparatus. The adoption of X-Window enables remote display and input to a thermal analysis apparatus through an X server on the network. The control and monitor with the thermal analysis apparatus has been enabled at a sitting room by setting up an X server within a sitting room and a thermal analysis apparatus other than the user interface within the laboratory with a network medium connected there between.

However, the conventional technology includes the following problems.

(1) Because all the displays and inputs related to measurement are carried out at a remote site, there may be encountered inconvenience in the measuring technique. For example, the procedure of TG before starting measurement is as follows.

(a) Setting a sample pan and a reference pan on a sensor.
(b) Waiting for stabilization of a TG signal and, after stabilization, instructing that the TG signal is currently 0 mg to the thermal analysis apparatus.
(c) Putting a sample in the sample pan.
(d) Waiting for stabilization of the TG signal, and after stabilization, instructing the thermal analysis apparatus to weigh the sample.
(e) Inputting a temperature program and so on to the thermal analysis apparatus.
(f) Providing a measurement start instruction to the thermal analysis apparatus.

Among these, steps (a) and (c) are operations conducted at the sensor of the thermal analysis apparatus, whereas steps (b), (d), (e) and (f) are operations performed through the user interface of the thermal analysis apparatus. It is therefore extremely inconvenient if the user interface is placed at a remote site.

(2) Because even one input to the keyboard, mouse movement or a slight display change is sent via the network medium, communication is done at all times and the amount of communication data becomes enormous.

It is an object of the present invention to provide a thermal analysis apparatus in which a user interface is operated close to a sensor and data is remotely monitored while suppressing the amount of communication data on the network medium.

DISCLOSURE OF THE INVENTION

The present invention has been developed in order to solve the above problem, and has principal constituent elements comprising a heating oven, a temperature sensor, a physical amount sensor, heating oven control means, data accumulating means, data transmission request receiving means, data transmitting means, measurement user interface means, data specifying means, data transmission request transmitting means, data receiving means, data display means, monitor user interface means and a network medium.

The apparatus is structured such that a measuring section and a monitor section are connected by the network medium wherein the measurement user interface is placed around the heating oven so that data at an arbitrary time point is monitored at a remote site. Accordingly, inconvenience encountered when starting measurement is eliminated which is encountered in a case that the measurement interface is located at a remote site.

Also, the amount of communication data is decreased by the following two effects.

(1) Because data is sent onto the network medium when required, the frequency of communications is decreased as compared with the conventional example.

(2) Communication content is changed from user interface operation with extremely high concreteness into data as abstract one.

BEST MODE FOR CARRYING OUT THE INVENTION

An embodiment of the present invention will be explained hereunder based on the drawings.

Figure 1:
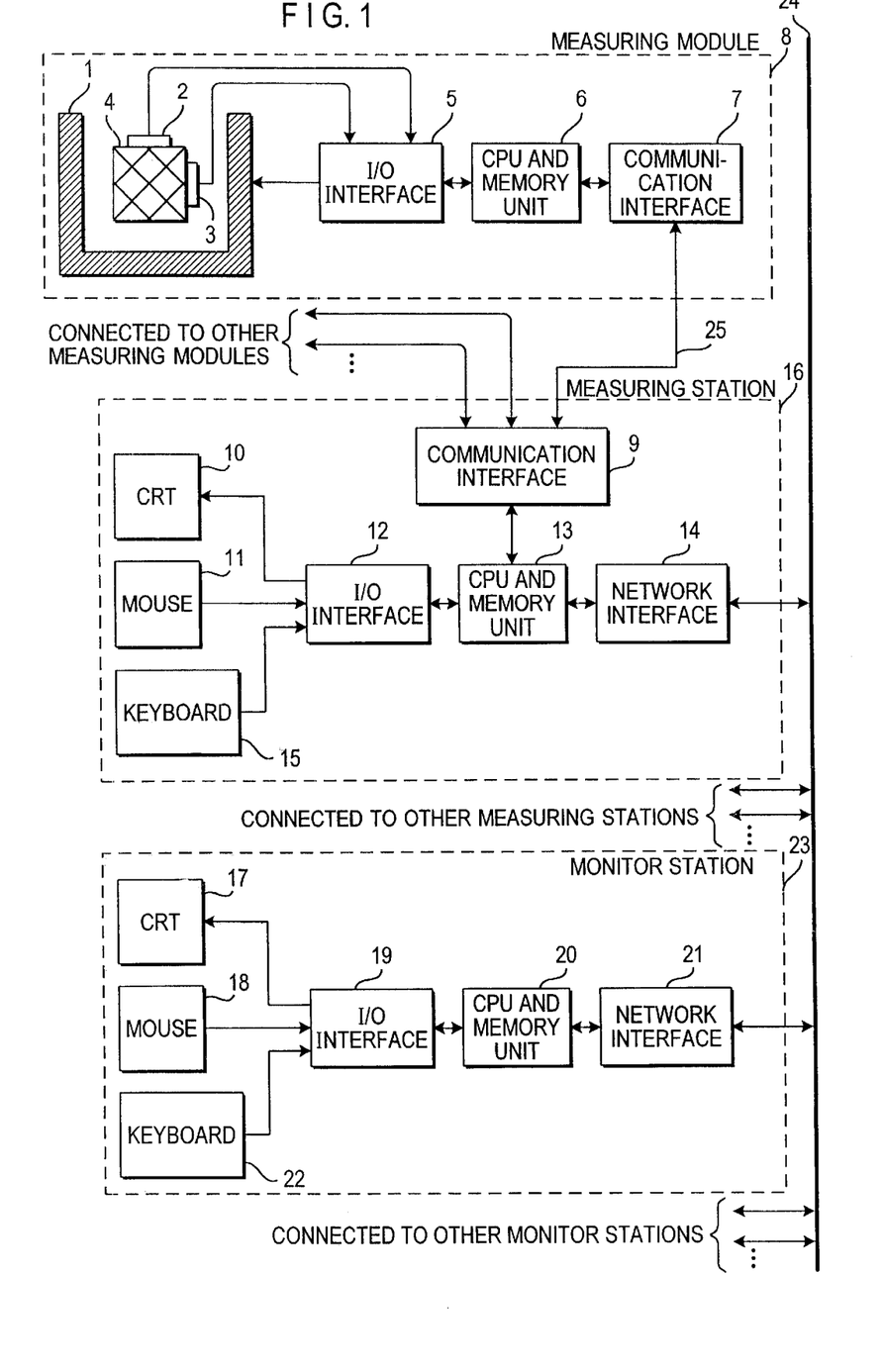
FIG. 1 is a hardware configuration in an embodiment of the present invention.

FIG. 1 is a hardware structure in the embodiment of the present invention.

A measuring module 8 heats up the sample 4 according to instructions received from a measuring station 16 and detects the temperature and physical amount of the sample 4, and transmits the data to the measuring station 16.

Figure 2:
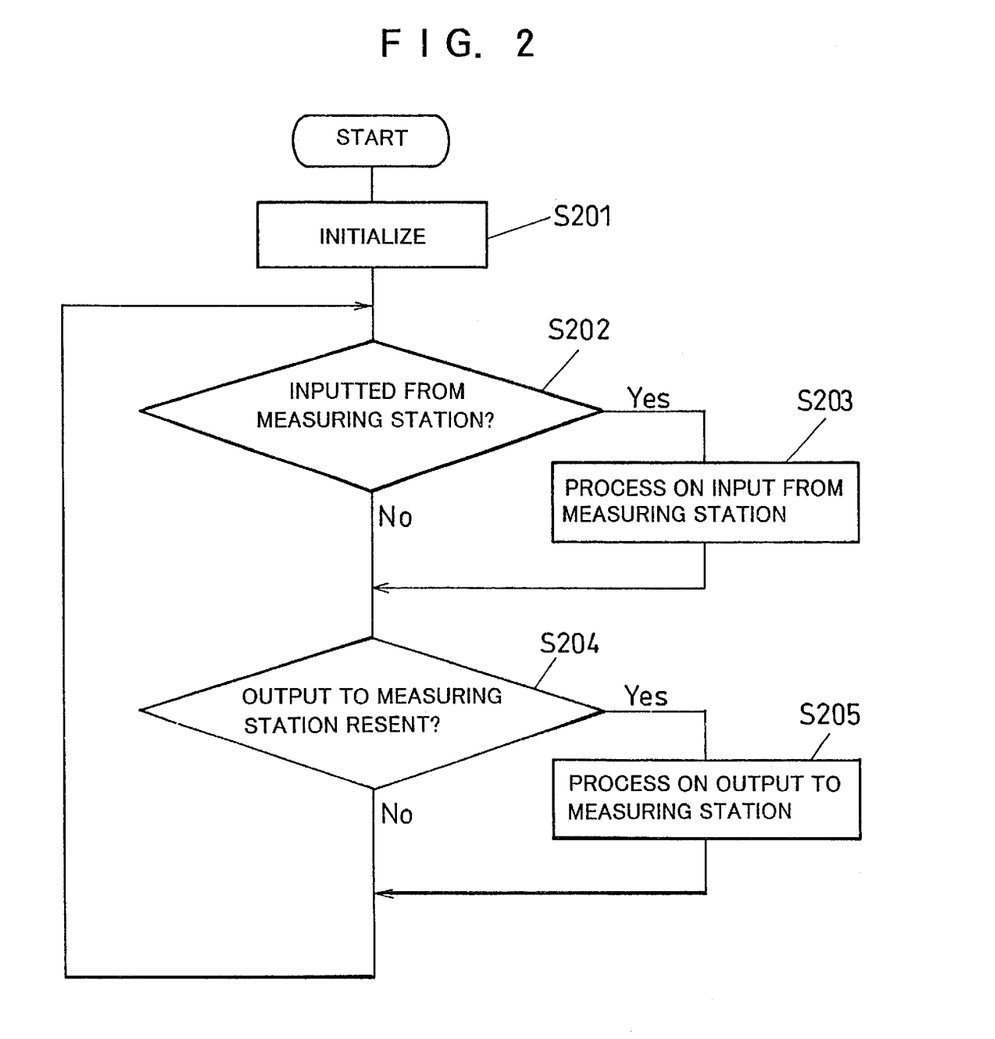
FIG. 2 is a flowchart of principal software to be executed by a measuring module central processor and memory unit in the embodiment of the present invention.

The measuring module 8 performs its function according to software shown in FIG. 2.

The user of the thermal analysis apparatus places a sample 4 in a heating oven 1. The sample 4 is detected for variation in temperature by a temperature sensor 2, and the sample 4 is monitored for a change in physical amount by a physical amount sensor 3. The physical amount sensor 3, if for example DSC, detects movement of heat quantity for the sample 4, if TG weight variation of the sample, and if TMA shape variation of the sample 4. The heating oven 1, the temperature sensor 2 and the physical sensor 3 are connected to a measuring module input/output interface 5, and are further connected to a measuring module central processor and memory unit 6. The temperature control of the heating oven 1 is performed by the measuring module central processor and memory unit 6 connected to the heating oven through the measuring module input/output interface 5. Also, the measuring module central processor and memory unit 6 is connected to a measuring station 16 through a measuring module communication interface 7.

The measuring station 16 performs processing on instructions to the user interface about measurement and to a plurality of measuring modules 8, data accumulation, and data transmission request and data transmission with a monitor station 23, which uses so-called a personal computer or work station. The measuring station 16 performs its function by use of a general purpose operating system, such as Windows, Windows-NT and UNIX, and software shown in FIG. 3.

The user of the thermal analysis apparatus effects dialogue through a measuring station mouse 11, a measuring station keyboard 15 and a measuring station CRT 10, to give instructions to the measuring module 8. These devices are connected to the measuring station central processor and memory unit 13 through the measuring station input/output interface 12.

Also, the measuring station central processor and memory unit 13 is connected to a plurality of measuring modules 8 through a measuring station communication interface 9 and a measuring module-measuring station communication path 25. The measuring module-measuring station communication path 25 may be any of the well known general purpose communication paths such as RS-232-C, GP-IB and SCSI.

The data transmission request and the data transmission to and from the monitor station 23 are made through a measuring station network interface 14 and a network medium 24 that are connected to the measuring station central processor unit 13. The network medium 24 may be any of the known general purpose network mediums, such as Ethernet, FDDI and TokenRing.

Figure 4:
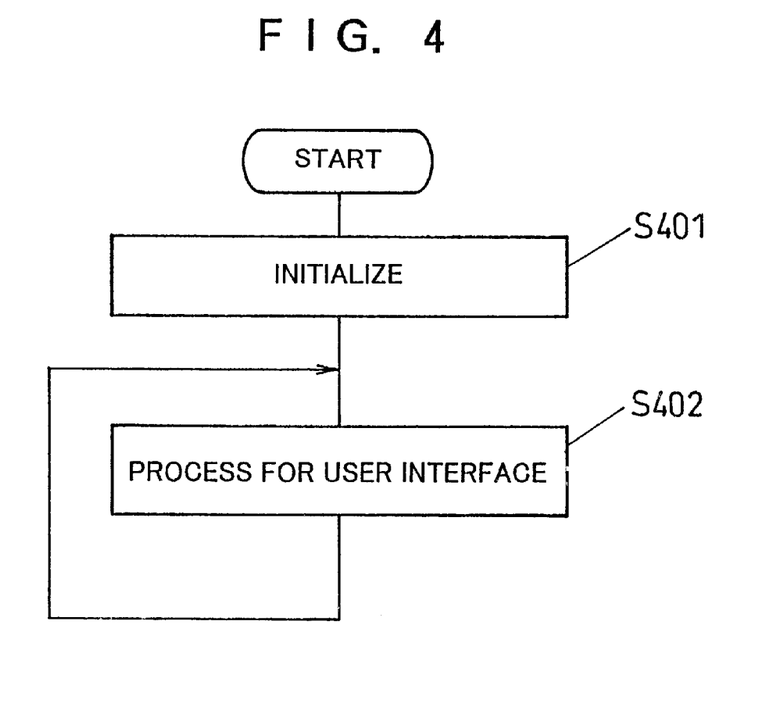
FIG. 4 is a flowchart of principal software to be executed by a monitor station central processor and memory unit in the embodiment of the present invention.
Figure 5:
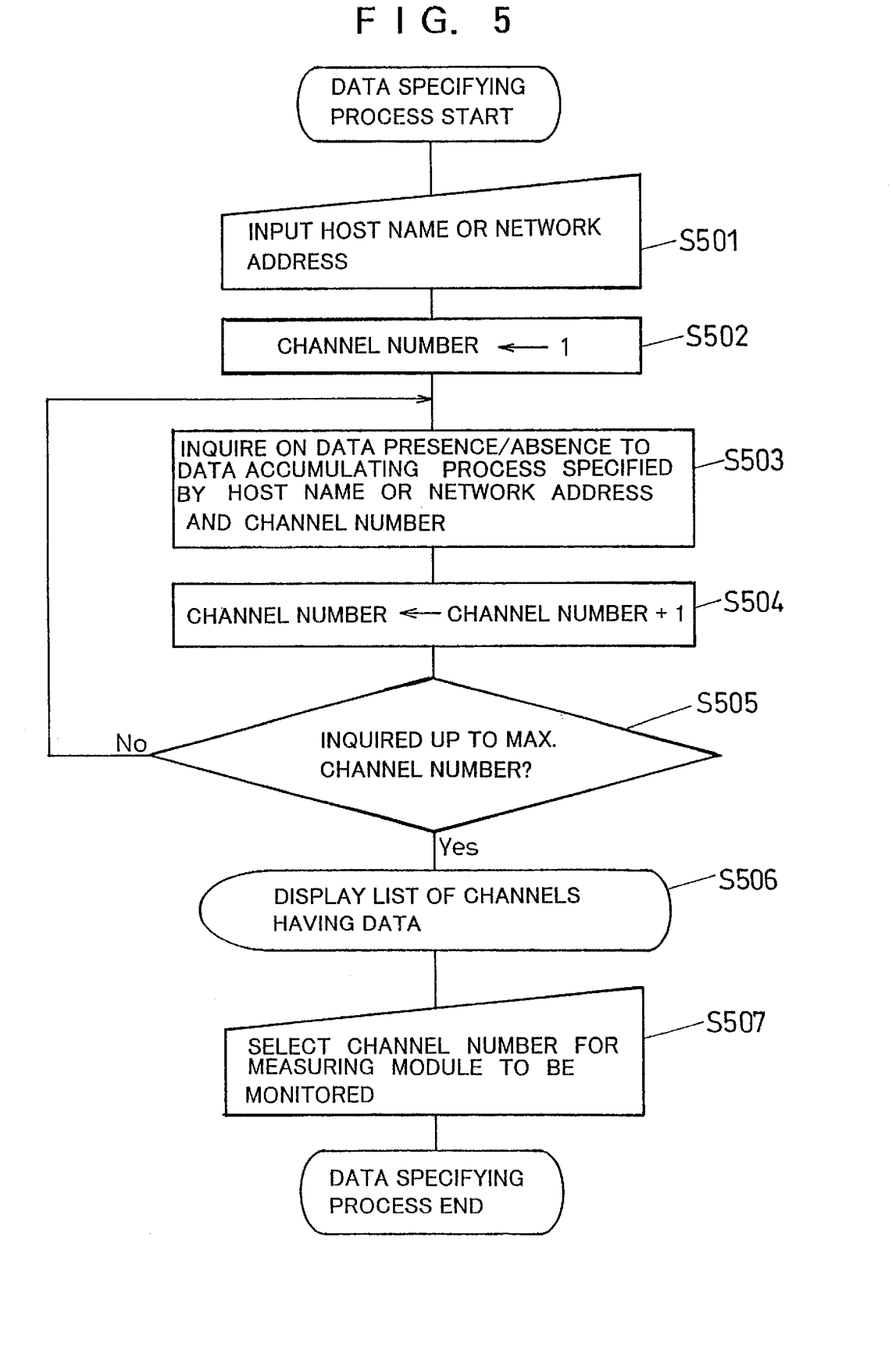
FIG. 5 is a flowchart of a data specifying process subroutine called from the principal software for the monitor station in the embodiment of the present invention.
Figure 6:
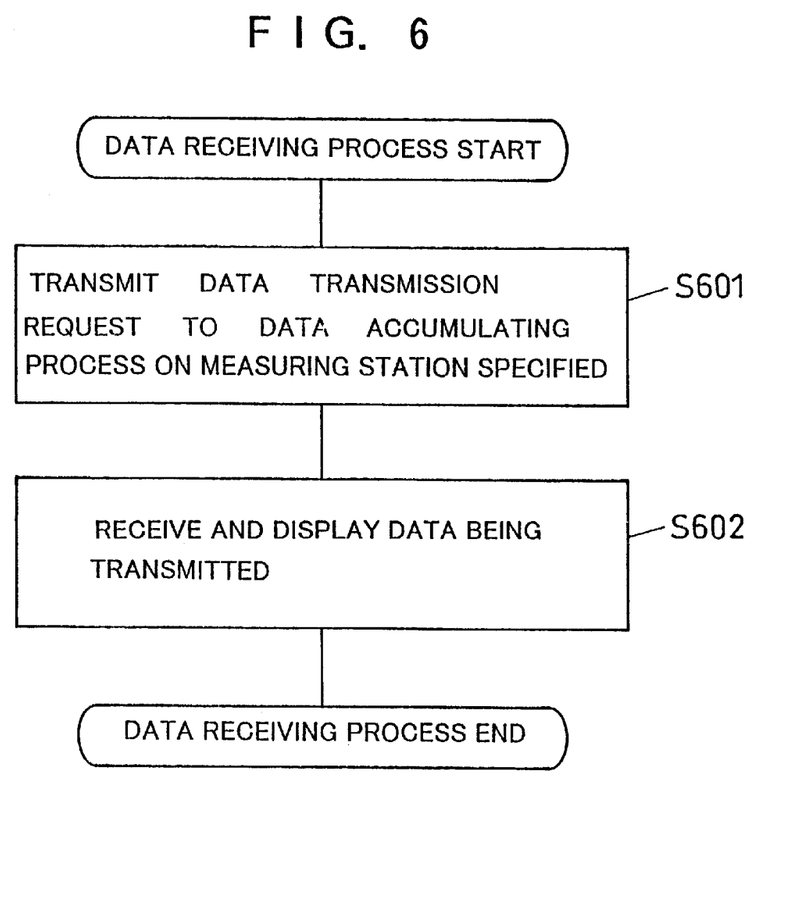
FIG. 6 is a flowchart of a data receiving process subroutine called from the principal software for the monitor station in the embodiment of the present invention.

The monitor station 23 is used to specify data to be monitored and to monitor the data, and uses a so-called personal computer or work station. The monitor station 23 effects its function through a general purpose operating system, such as Windows, Windows-NT or UNIX, and software as shown in FIG. 4, FIG. 5 and FIG. 6.

The user of the thermal analysis apparatus specifies data to be monitored through a monitor station mouse 18, monitor station keyboard 22 and monitor station CRT 17 to monitor the data. These devices are connected to a monitor station central processor and memory unit 20 through a monitor station input/output interface 19.

Also, the monitor station central processor and memory unit 20 is connected to a plurality of measuring stations 16 through a monitor station network interface 21 and network medium 24.

FIG. 2 is a flowchart of software to be executed on the measuring module central processor and memory medium 6.

First, initialization is made in order to prepare an operating environment [S201]. Then, If there is an input from the measuring station 16 through the measuring module communication interface 7 [S202], the input is processed [S203]. If there is an output to the measuring station 16 [S204], the output is processed [S205]. Transmission is made to the measuring station 16 via the measuring module interface 7.

The inputs from the measuring station 16 include the following:

temperature program instructions to start and end a measurement.

To reflect these inputs in control of the heating oven is a process [S203] is used. The output to the measuring station 16 includes the following:

data (set of a detected temperature and a physical amount)

state of the measuring module 8

To convert the signals of the temperature sensor 2 and the physical amount sensor 3 and the state of measuring module 8 into a communicable form is a process [S205] is used.

Figure 3:
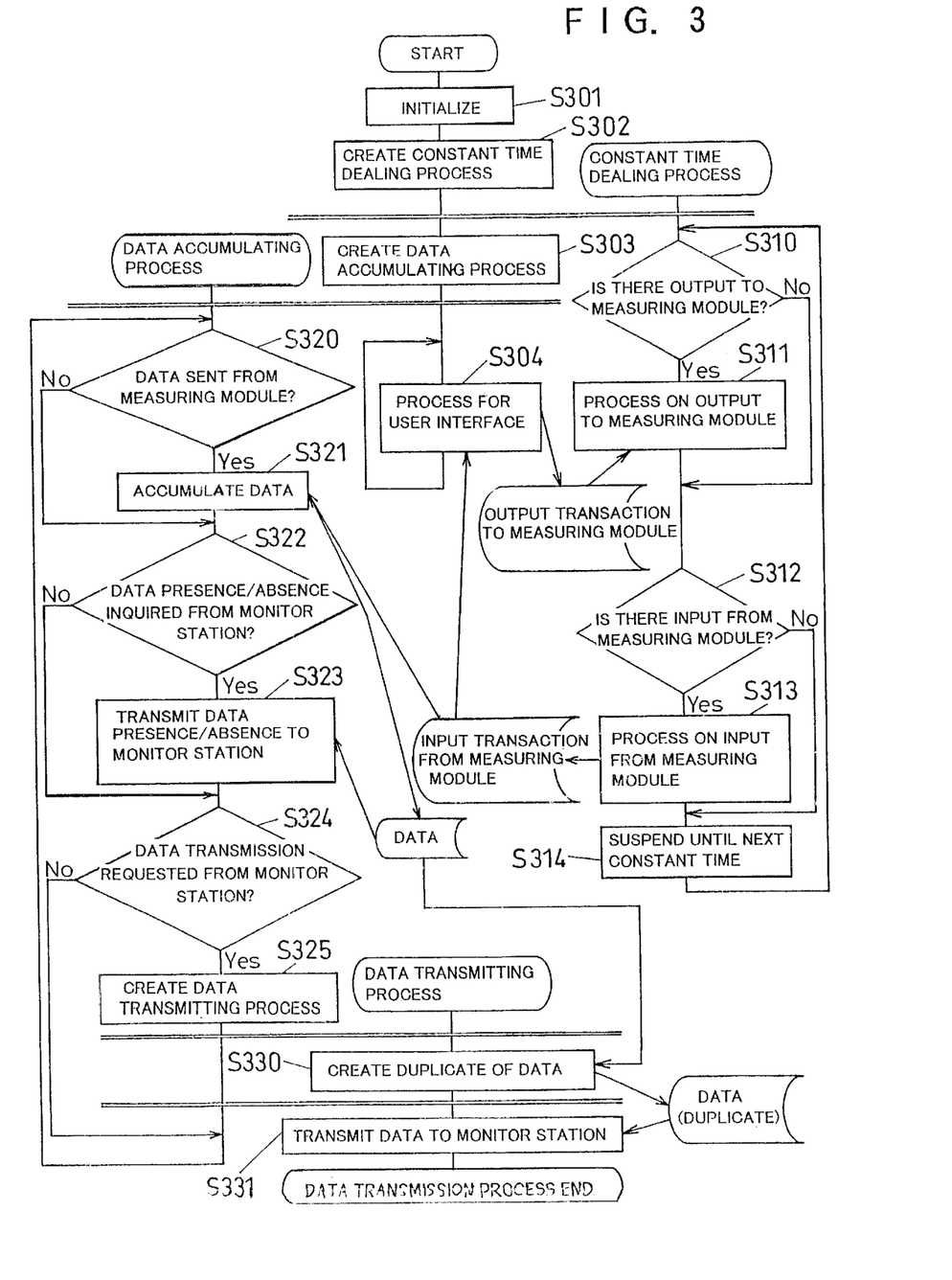
FIG. 3 is a flowchart of principal software to be executed by a measuring station central processor and memory unit in the embodiment of the present invention.

FIG. 3 is a flowchart of software to be executed on the measuring station central processor and memory unit 13, which is executed for each measuring module 8 to be connected. That is, when there are a plurality of measuring modules 8 to be connected, the independent software as shown in FIG. 3 is being executed on the measuring station central processor and memory unit 13.

This software performs initialization to adjust an operating environment [S301], and generate a constant time dealing process to effect constant time treatments at an appropriate interval [S302].

The constant time dealing process performs communication with the measuring module 8 through the measuring station communication interface 9. In the FIG. 3 software, if there is data content to be output to the measuring module 8, the content is placed in an output transaction. When the input content from the measuring module 8 is to be referred to, reference is made to the input transaction. Due to this, the constant time dealing process, if there is an output to the measuring module 8 [S310], outputs the content of the output transaction to the measuring module 8 [S311]. If there is an input from the measuring module 8 [S312], the input is processed to place the content in the input transaction [S313].

In this manner, the communication with the measuring module 8 is processed by an independent process thereby preventing errors from occurring in communication requiring real time characteristics.

On the other hand, a main process generates a constant time dealing process and thereafter generates a data accumulating process [S303].

The data accumulating process makes reference to an input transaction. If data is sent from the measuring module 8 [S320], the data is taken out of the input transaction to accumulate it at an accumulation site [S321]. Also, if there is an inquiry on the presence or absence of data from the monitor station 23 [S322], it is processed [S323]. If there is a data transmission request from the monitor station 23 [S324], it is processed [S325]. (The detail of [S322]–[S325] and [S330]–[S331] is stated later.)

In this manner, the data accumulating process is processed by the independent process whereby data pick-up errors are prevented to cope with inquiries or the like that are asynchronous with the main process from the monitor station 23.

The main process thus generates the data accumulating process then processes for the user interface about measurement [S304]. The instruction or setting on measurement given by the user is processed here, and appropriate content is placed in an output transaction thereby being delivered to the measuring module 8. Also, the state of the measuring module 8 is output to the measuring user interface by processing the input transaction [S304].

FIG. 4 is a flowchart of software to be executed on the monitor station central processor and memory unit 20. This software is initialized to adjust an operating environment [S401], and processes on the user interface about monitoring [S402]. In this processing on the user interface, data to be monitored is specified and data is received.

Figure 7:
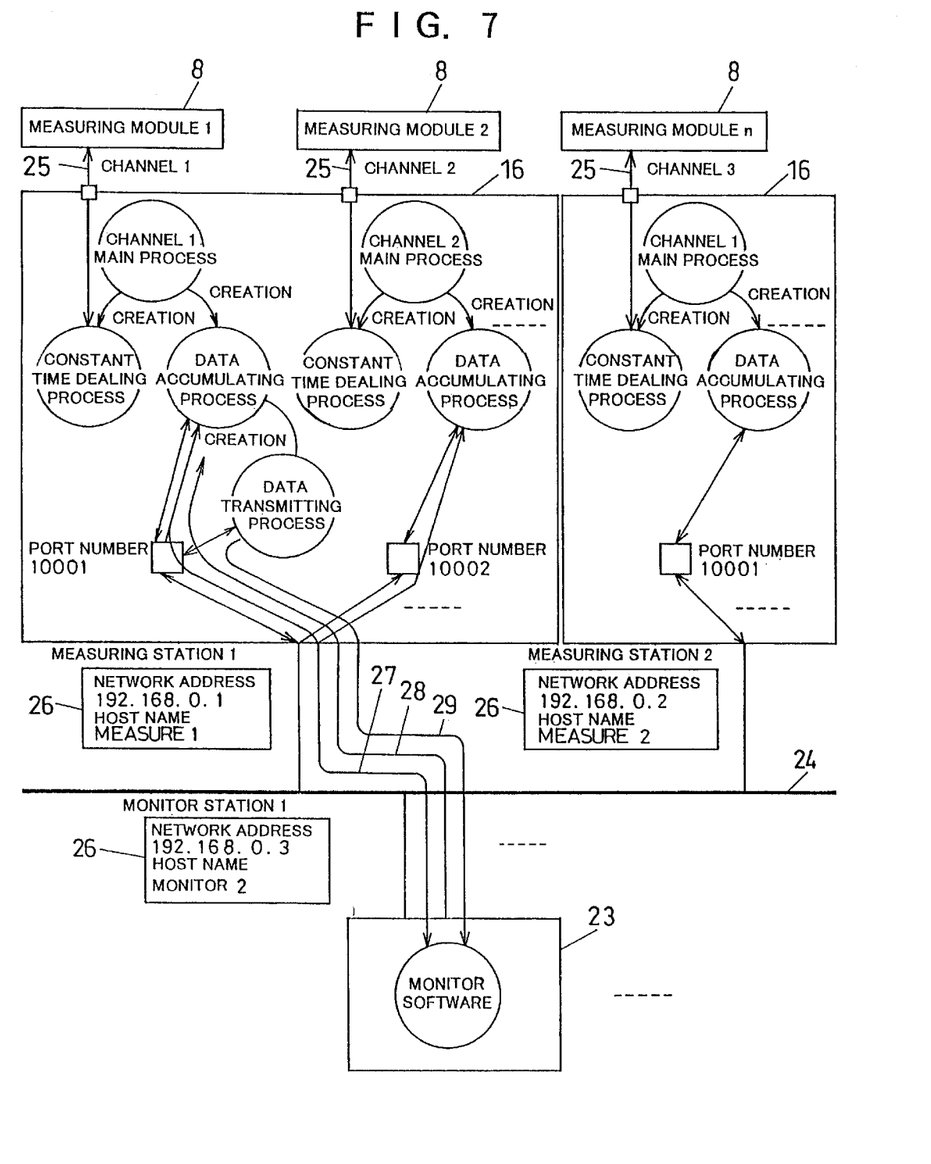
FIG. 7 is an explanatory chart of a data specifying means and data transmitting means in the embodiment of the present invention.

Now explanation is made on the means to specify data to be monitored and receive data in the embodiment of the present invention, with reference to FIG. 5 to FIG. 7.

First, the user specifies on which data is to be monitored. Due to this, an instruction is made to the user interface of the monitor station 23. By processing on the user interface of the monitor station 23 [S402], a data specifying process subroutine in FIG. 5 is called out.

The data specifying process subroutine thus called out ask for inputting of a host name or a network address to the user, and receives an input [S501]. Those connected to the network medium 24 are assigned with a network address and host name peculiar to each of the stations as shown at 26 in FIG. 7. By assigning this, determination is made as to in which measuring station 16 data is to be monitored.

Because a plurality of measuring modules 8 are connected to the measuring station 16 as shown in FIG. 7, a determination is made as to in which measuring module 8 data is next to be monitored. For this reason, the data specifying process subroutine inquires about the presence or absence of data in each measuring module 8 connected to the specified measuring station 16 to the measuring station 16. The measuring station communication interface 9 is set with a channel number for each connection port. Also, the network has a configuration called port numbers to discriminate a connection port for each software routine, in order to share one network by a multiplicity of software routines. By combining a port number with a channel number, inquiry is made for a data accumulating process corresponding to each measuring module 8.

For example, the software of the present invention uses port numbers beginning from a port number 10000 wherein a predefined condition is set wherein 10000 added with a channel number is a port number of a network connection port for each data accumulating process. Inquires are made up to a channel number having a possibility of connection as in [S5002]–[S505].

For example, when inquiring to each data accumulating process on the measuring station 16 at a network address 192. 168.0.1, the network connection port inquired, as in the path 27 of inquiry on the presence and absence of data to each data accumulating process in FIG. 7, is (network address: port number)

192.168.0.1: 10001

192.168.0.1: 10002.

Each data accumulating process inquired sends back information as to the presence or absence of data through [S322]–[S323].

If inquires have been made up to a maximum channel number to be possibly connected, the data specifying process subroutine displays a channel number through which the presence of data is responded [S506] and asks the user for selecting as to which channel number of a measuring module 8 is to be monitored [S507].

If data to be monitored is specified, the software on the monitor station 23 calls a data receiving process subroutine following a data specifying process subroutine.

The data receiving process subroutine sends a data transmitting request onto a network connecting port of the specified data accumulating process (192.168.0.1: 10001 in the case of a data transmission request path 28 for the specified data accumulating process in FIG. 7) [S601].

For detecting a data transmission request [S324], a data transmitting process is created [S325].

The data transmission process creates a duplicate of data [S330]. By making a data duplicate, it can be avoided to prevent the data in the data accumulating process from accumulating without being conscious to ensure that the data transmitting process keeps consistency on the accumulated data.

Then, the data transmitting process sends data to the monitor station 23 as through the data transmission path 29 to the specified data accumulating process in FIG. 7 [S331].

The data receiving process subroutine receives sent data and displays the data [S602].

In this manner, in the embodiment of the present invention data monitoring is carried out at a remote site.

Now other embodiments of the present invention will be explained.

It was already stated that measurement takes time as a thermal analysis characteristic. However, because of this characteristic there are cases where a multiplicity of measuring modules 8 are employed to conduct simultaneous measurements in order to shorten the time. At this time, there is a case where a plurality of measuring stations 16 are simultaneously used besides one measuring station 16. In the above embodiment, because a measuring station 16 is first specified and thereafter a list is displayed, there is a case where difficulty is encountered in dealing with a multiplicity of measuring stations 16. This is improved in the below first and second embodiments.

Also, although the above embodiment may use much resource, this is improved in the third and fourth embodiments.

The first one is on another embodiment of a data specifying means.

Figure 8:
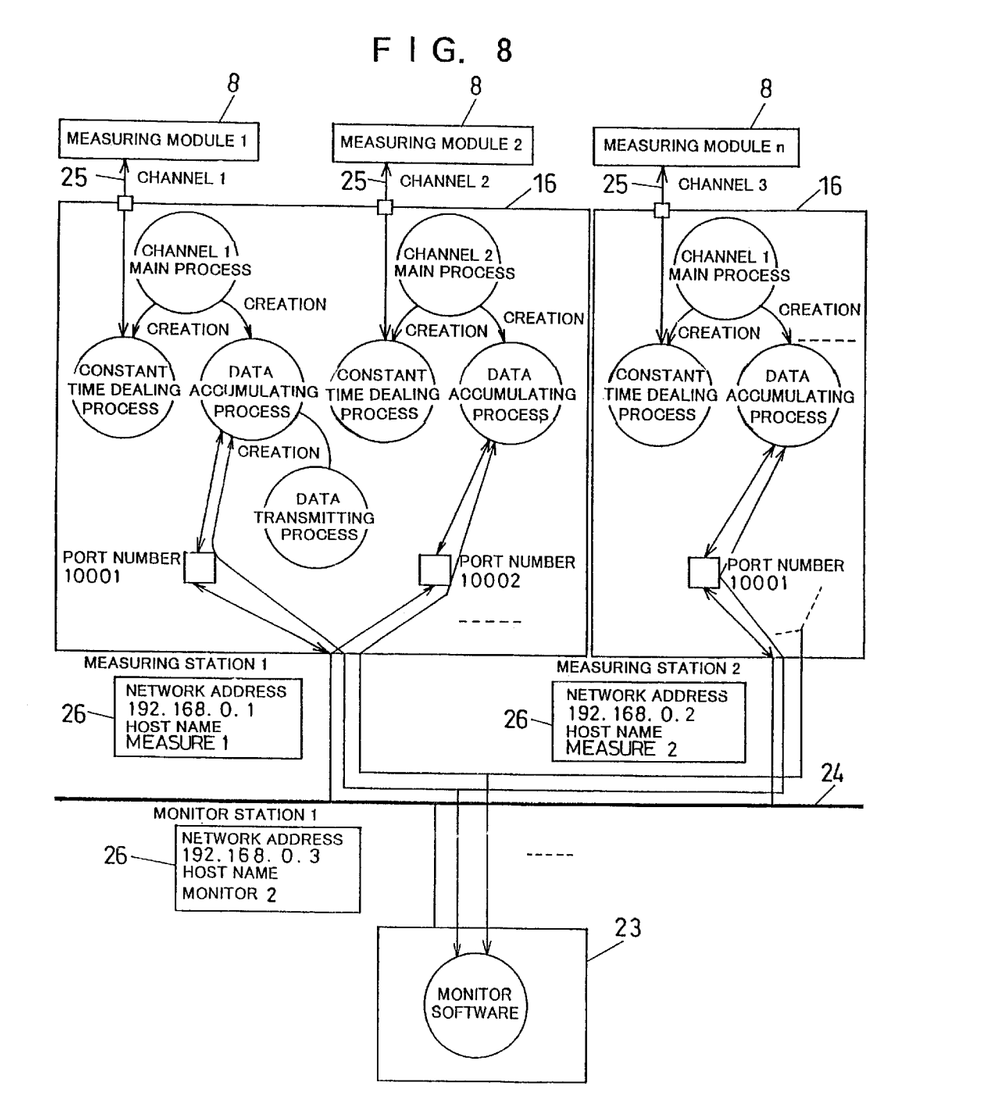
FIG. 8 is an explanatory chart of a data specifying means in another embodiment utilizing a broadcast function of the present invention.

FIG. 8 is an explanatory chart of another embodiment utilizing a broadcast function in the data specifying means.

There are some networks that support broadcast functions. For example, in TCP/IP if transmission is made by designating a network address 192.168.0.255, then transmission is performed to all ones connected to the network.

If this network address is used to inquire, as in 30, 31 in FIG. 8, onto each channel by 192.168.0.255: 10001

192.168.0.255: 10002,

[S501] in FIG. 5 can be omitted.

This method has an advantage in that the channel numbers for all the measuring stations having data on the network can be displayed without previously specifying measuring stations 16.

However, there is also a disadvantage in that there is an increase in the communication amount of data on the network medium 24 because, inquiries are sent to all stations connected to the network including those other than the measuring stations.

The second is on another embodiment of a data specifying means.

Figure 9:
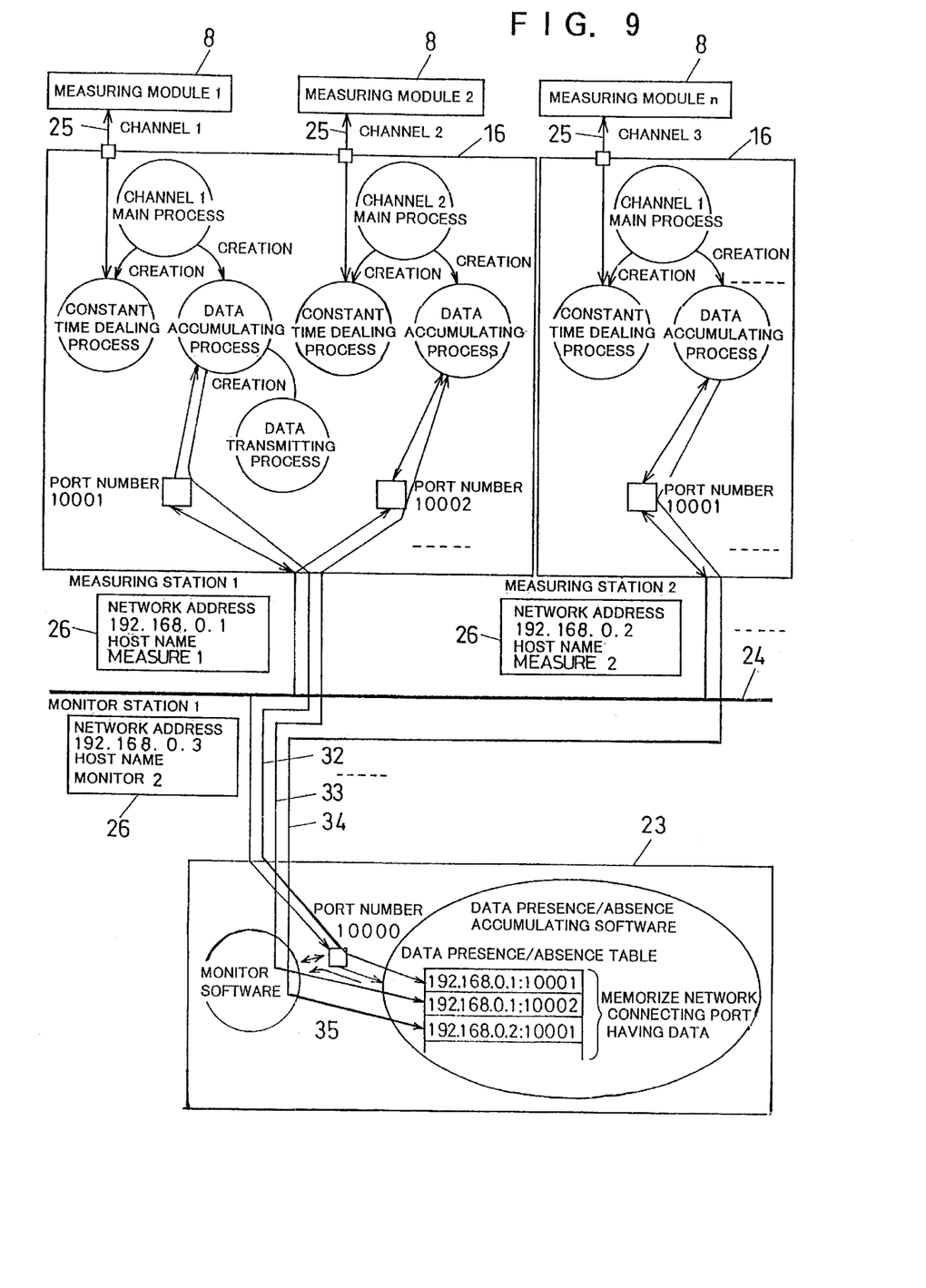
FIG. 9 is an explanatory chart of a data specifying means in another embodiment prepared with software for accumulating the presence and absence of data of the present invention.

FIG. 9 is an explanatory chart of another embodiment prepared with software for accumulating the presence or absence of data.

Prepared is one software for accumulating the presence or absence of data. The operation site may be on any of the measuring station 16 or monitor station 23, or on a not-related computer other than those. The data accumulated process is previously taught of a network address at a site where software for accumulating the presence or absence of data is operating. The presence or absence is periodically sent to the data presence/absence accumulating software as in 32, 33 and 34 in FIG. 9. Due to this, created is a table of network connecting ports to data accumulating processes in which data exists. The monitor software is sent by the table of network connecting ports to data accumulating processes as in 35 in FIG. 9, thereby displaying all the channel numbers having data on the network without effecting [S501]–[S505] in FIG. 5.

The advantage of this method lies in that all measuring station channel numbers on the network can be displayed with less communication amount on the network medium 24 and reduced time.

However, there is a disadvantage in that resources (central processor and memory unit) are required for the data presence/absence software.

The third is on anther embodiment of a data transmitting means without preventing the data accumulating means.

Figure 10:
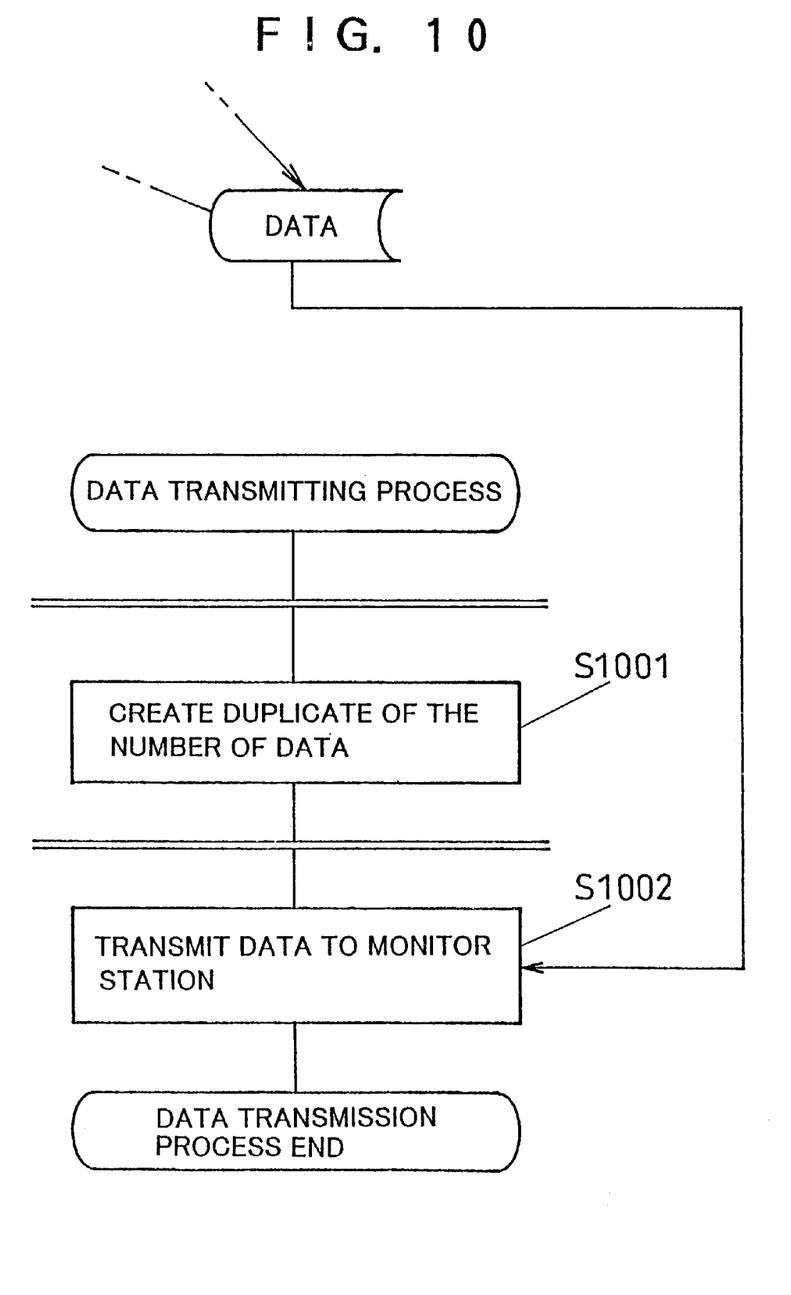
FIG. 10 is a flowchart of a data transmitting process in another embodiment of a means to perform data transmission without preventing the data accumulating means of the present invention.

FIG. 10 is an improvement over [S330]–[S331] in FIG. 3, wherein the data duplicate creation in [S330] is changed to creating a duplicate on the number of data in [S1001]. Because a data accumulating program merely makes addition to the data, the number of the data up to this time is duplicated to thereby transmit the data to the monitor station 23 without duplicating the data [S1002].

The advantage of this method lies in that the memory unit can be saved.

However, there is a defect in that consideration should be paid not to lose data in the course of data transmission.

The fourth is on another embodiment utilizing a measuring module station combining the measuring module 8 with the measuring station 16.

Figure 11:
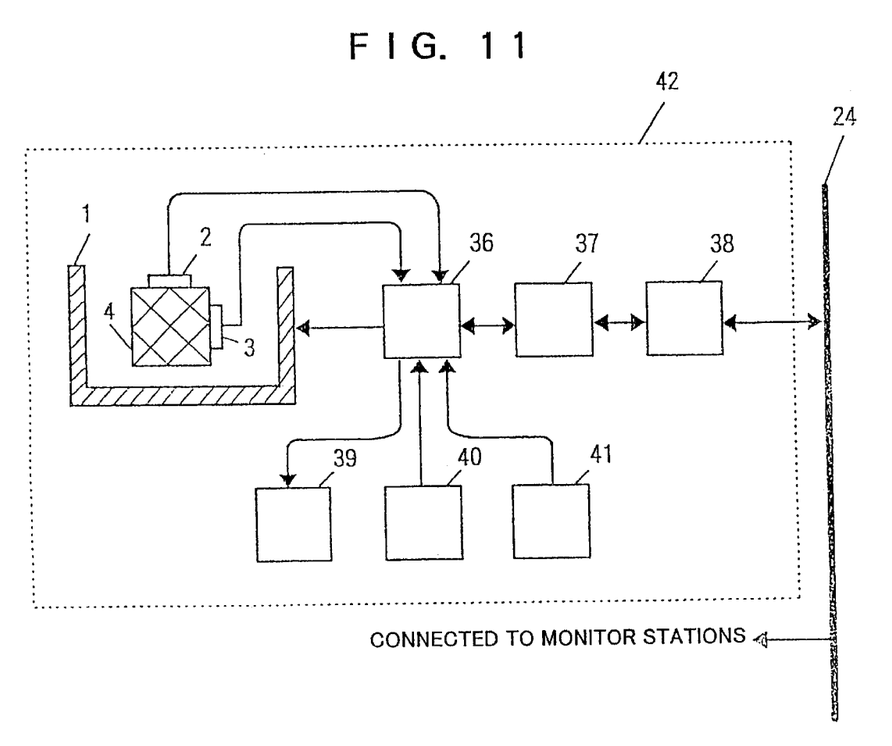
FIG. 11 is a hardware configuration in another embodiment according to a measuring module station of the present invention.

FIG. 11 is a hardware configuration of a measuring module station 42 having a combination of the measuring module 8 and the measuring station 16. The software of FIG. 2 and FIG. 3 operates on the measuring module station central processor and memory unit 37.

The advantage of this method lies in that t is possible to reduce cost when one thermal analysis technique is employed.

However, there is also a disadvantage in that there is an increase in cost when a plurality of thermal analysis techniques are used.

What is claimed is:

1. A thermal analysis apparatus, comprising:
   one or more heating ovens for heating a sample;
   a temperature sensor for each heating oven for detecting one of a temperature of the sample or a temperature in the vicinity of the sample;
   a physical amount sensor for each heating oven for detecting a change in a physical characteristic of the sample in response to one of a temperature change of the sample or a temperature change in the vicinity of the sample;
   heating oven control means for controlling a temperature of each heating oven;
   data accumulating means for accumulating data signals detected by each temperature sensor and each physical amount sensor;
   data transmission request signal receiving means for receiving a data transmission request signal to request data transmission;
   data transmitting means for transmitting data according to the data transmission request signal;
   measurement user interface means for inputting instructions to the heating oven control means and the data accumulating means;
   data specifying means for selecting specified data to be received through a network medium;
   data transmission request signal transmitting means for transmitting a data transmission request for the selected data;
   data receiving means for receiving data;
   display means for displaying received data;
   monitor user interface means for supplying instructions to the data specifying means, the data transmission request signal transmitting means and the data receiving means; and
   a network medium for connecting between the data transmission request signal receiving means, the data transmission request signal transmitting means and the data transmitting means.

2. A thermal analysis apparatus according to claim 1; wherein the data transmission request signal transmitting means includes means for inquiring as to the presence or absence of data to the data accumulating means to display results thereof on the display means in response to a selection by a user.

3. A thermal analysis apparatus according to claim 1; wherein the data accumulating means comprises a plurality of data accumulating means connected to each temperature sensor and each physical amount sensor and connected over the network medium to the data specifying means, and the data specifying means includes broadcast means for inquiring as to the presence or absence of data to each data accumulating means connected to the network medium and displaying results of the inquiry for selection by a user.

4. A thermal analysis apparatus according to claim 1; further comprising a data presence/absence accumulating means for holding a notification of the presence or absence of data from the data accumulating means, and the data specifying means includes means for inquiring as to the presence or absence of data from the data presence/absence accumulating means and displaying results of the inquiry for selection by a user.

5. A thermal analysis apparatus according to claim 1; wherein the data transmitting means creates a duplicate of data to be transmitted and performs transmission using the duplicate.

6. A thermal analysis apparatus according to claim 1; wherein the data transmitting means creates a duplicate of data and data to be used is shared with the data accumulating means and data transmission is performed using the duplicate.

7. A thermal analysis apparatus according to claim 1; wherein each physical amount sensor comprises a detector for detecting movement of heat quantity of the sample in response to temperature variation for performing DSC analysis.

8. A thermal analysis apparatus according to claim 1; wherein each physical amount sensor comprises a detector for detecting weight variation of the sample in response to temperature variation for performing TG analysis.

9. A thermal analysis apparatus according to claim 1; wherein each physical amount sensor comprises a detector for detecting shape variation of the sample in response to temperature variation for performing TG analysis.

10. A thermal analysis apparatus according to claim 1; wherein the network medium comprises an ethernet, FDDI or token ring network medium.

11. A thermal analysis apparatus according to claim 1; wherein each heating oven, temperature sensor, physical amount sensor and the heating oven control means comprise a measuring module for heating the sample according to instructions received from a measuring station, monitoring the sample for change in temperature and physical characteristics, and transmitting monitored results to the measuring station.

12. A thermal analysis apparatus according to claim 11; wherein the measuring module is contained in a room where thermal analysis is performed on the sample.

13. A thermal analysis apparatus according to claim 12; wherein the measuring station comprises the data accumulating means, the data transmission request receiving means, the data transmitting means, and the measurement user interface means.

14. A thermal analysis apparatus according to claim 13; wherein a plurality of the measuring modules are connected to the measuring station.

15. A thermal analysis apparatus according to claim 14; wherein a plurality of the measuring stations are connected to each of the plurality of measuring modules by means of a direct connection without using the network medium, and the data accumulating means comprises a separate data accumulating means for each of the measuring modules, each data accumulating means being assigned a consecutive port number so that data from each of the measuring modules is accessible.

16. A thermal analysis apparatus according to claim 13; wherein the measuring station is located nearby the room in which thermal analysis is performed on the sample; and the measuring module and the measuring station each further comprise a communication interface for communicating with each other without using the network medium.

17. A thermal analysis apparatus according to claim 16; wherein the data specifying means, the data transmission request transmitting means, the data receiving means, the display means and the monitor user interface means comprise a monitoring station.

18. A thermal analysis apparatus according to claim 17; wherein the monitoring station is located remotely from the room in which thermal analysis is performed on the sample, and is connected to the measuring station over the network medium.

19. A thermal analysis apparatus according to claim 18; wherein a plurality of the measuring stations are connected to each of a plurality of measuring modules by means of a direct connection without using the network medium, and one or more of the measuring stations and the plurality of measuring modules are connected over the network medium.

20. A thermal analysis apparatus according to claim 19; wherein the data accumulating means comprises a separate data accumulating means for each of the measuring modules, each data accumulating means being assigned a consecutive port number so that data from each of the measuring modules is accessible by the monitoring station.

21. A thermal analysis apparatus comprising: one or more measuring modules each comprising a heating oven for heating a sample, a temperature sensor for detecting one of a temperature of the sample and a temperature in the vicinity of the sample, a physical amount sensor for detecting a change in a physical characteristic of the sample in response to one of a temperature change of the sample or a temperature change in the vicinity of the sample, and heating oven control means for controlling a temperature of the heating oven; one or more measuring stations for providing instructions to the measuring modules to beat the sample and receiving monitored results from the measuring stations, each measuring station comprising data accumulating means for accumulating data signals detected by the temperature sensor and the physical amount sensor, data transmission request receiving means for receiving a data transmission request signal to request data transmission, data transmitting means for transmitting data according to the data transmission request signal, and measurement user interface means for inputting instructions to the heating oven control means and the data accumulating means; one or more monitor stations each comprising data specifying means for selecting specified data to be received through a network medium, data transmission request transmitting means for transmitting a data transmission request for the selected data, data receiving means for receiving data, display means for displaying received data, and monitor user interface means for supplying instructions to the data specifying means, the data transmission request signal transmitting means and the data receiving means; and a network medium for connecting between the measuring modules and the monitoring stations.

22. A thermal analysis apparatus according to claim 21; wherein the network medium connects between the data transmission request signal receiving means, the data transmission request signal transmitting means and the data transmitting means.

23. A thermal analysis apparatus comprising: a measuring module for heating a sample according to instructions, monitoring the sample for changes in temperature and physical characteristics, and transmitting monitored results; a measuring station for providing instructions to the measuring module to heat the sample and receiving monitored results from the measuring module; a monitoring station for selecting data to be received through a network medium, and receiving and displaying the selected data; and a network medium for connecting between the monitoring station and the measuring station.

24. A thermal analysis apparatus according to claim 23; wherein the measuring module comprises a heating oven for heating the sample, a temperature sensor for detecting one of a temperature of the sample and a temperature in the vicinity of the sample, a physical amount sensor for detecting a change in a physical characteristic of the sample in response to one of a temperature change of the sample or a temperature change in the vicinity of the sample, and heating oven control means for controlling a temperature of the heating oven.

25. A thermal analysis apparatus according to claim 24; wherein the measuring station comprises data accumulating means for accumulating data signals detected by the temperature sensor and the physical amount sensor, data transmission request receiving means for receiving a data transmission request signal to request data transmission, data transmitting means for transmitting data according to the data transmission request signal, and measurement user interface means for inputting instructions to the heating oven control means and the data accumulating means.

26. A thermal analysis apparatus according to claim 25; wherein the monitoring station comprises data specifying means for selecting specified data to be received through a network medium, data transmission request transmitting means for transmitting a data transmission request for the selected data, data receiving means for receiving data, display means for displaying received data, and monitor user interface means for supplying instructions to the data specifying means, the data transmission request signal transmitting means and the data receiving means.

27. A thermal analysis apparatus according to claim 26; wherein the network medium connects between the data transmission request signal receiving means, the data transmission request signal transmitting means and the data transmitting means.

* * * * *